United States Patent [19]

Streel

[11] 4,344,757
[45] Aug. 17, 1982

[54] IMPLANT A GEOMETRY VARIABLE

[76] Inventor: Robert Streel, rue Léon Mignon 21, 4000 Liège, Belgium

[21] Appl. No.: 148,308

[22] Filed: May 9, 1980

[30] Foreign Application Priority Data

May 17, 1979 [BE] Belgium .................. 6/46833

[51] Int. Cl.³ .............................................. A61C 8/00
[52] U.S. Cl. ................................................... 433/173
[58] Field of Search ......................... 433/220, 173, 176

[56] References Cited

U.S. PATENT DOCUMENTS 3,925,892 12/1975 Juillet ................................... 433/176
4,086,701 5/1978 Kawahara ........................... 433/174
4,103,422 8/1978 Weiss et al. ......................... 433/174

FOREIGN PATENT DOCUMENTS 2302715 6/1975 France ................................. 433/173

Primary Examiner—Robert Peshock
Attorney, Agent, or Firm—Martin A. Farber

[57] ABSTRACT

The base of the implant of the type composed of a perforated base, of a threaded shaft and is asymmetrical in relation to the shaft and the areas of the base, respectively the perforated parts, situated on both sides of the shaft are equal but of a different conformation.

7 Claims, 9 Drawing Figures

IMPLANT A GEOMETRY VARIABLE

The present invention concerns implant technique in dental surgery and is more particularly concerned with the so-called three-dimensional implants perfected and patented by Dr. Jean-Marc Juillet of Paris.

A three-dimensional implant, at present made of titanium, consists of a perforated base, with a threaded rod or shaft mounted perpendicularly on the base, and an abutment screwed on to the shaft in a regulable position, in order to permit the fixing of a tooth or part of a bridge.

The object of the invention is to adapt this type of implant to the particular configuration of certain areas, to facilitate its use as an artificial root and to improve its efficiency as an accessory pillar in fixed prosthesis.

A variable geometry implant according to the invention is characterised in that the base of the implant is asymmetrical in relation to the shaft and in that the areas of the said base, the perforated parts respectively, situated on both sides of the shaft, are equal but of a different conformation.

Also according to the invention the implantation is characterised in that the false stump is made up of two elements, one of which is in the shape of an inverted cone with a gingival apex and the other is of similar morphology to the current false stump but with reduced dimensions, the first element having at its centre, at the base of the cone a depression for the location of the second element which surmounts it.

Figure 1:
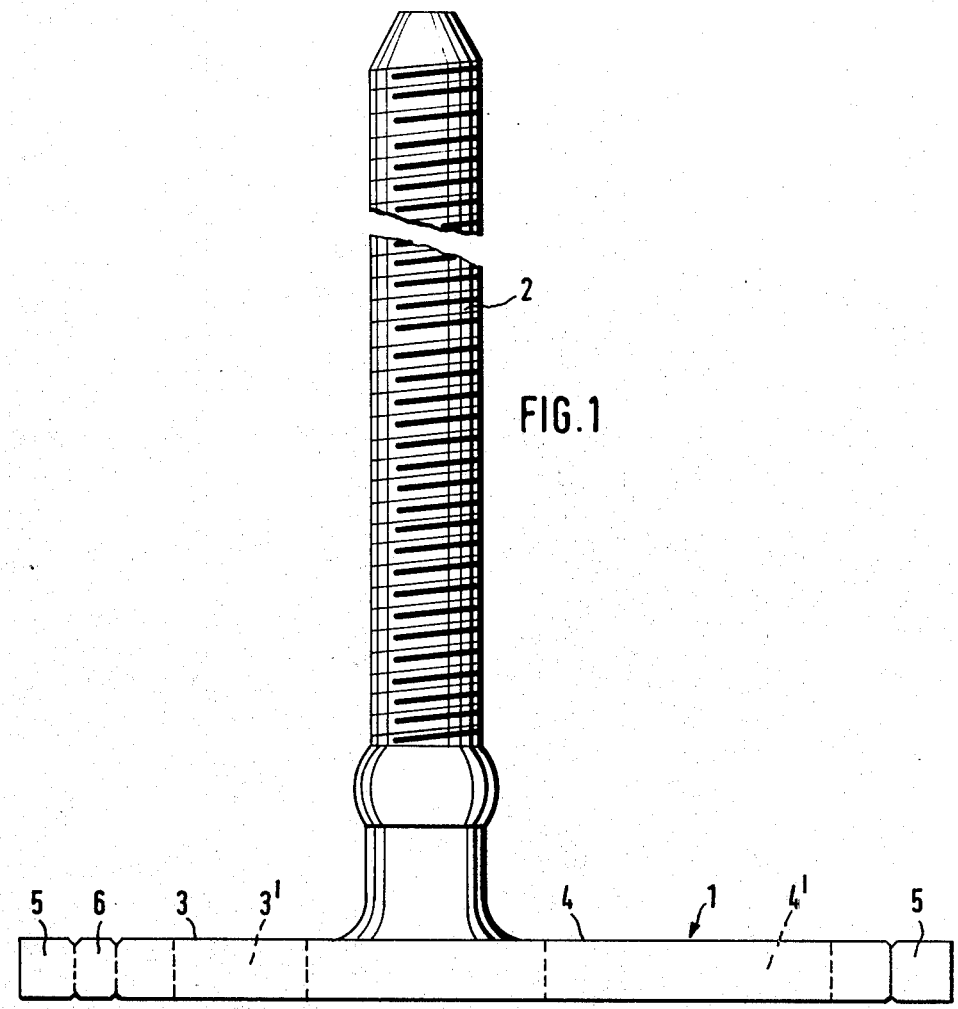
Figure 2:
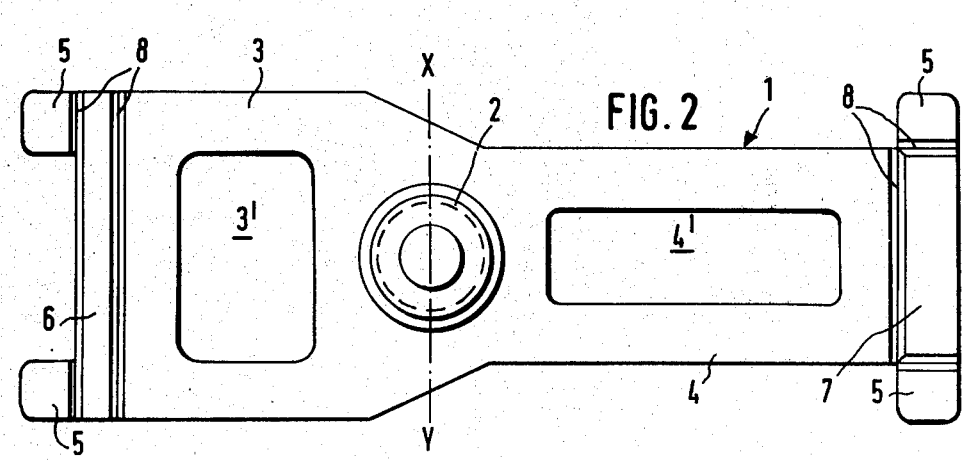
Figure 3:
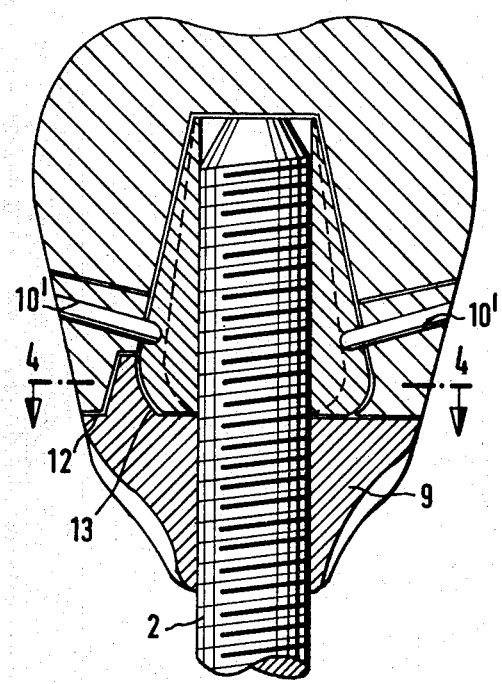
Figure 5:
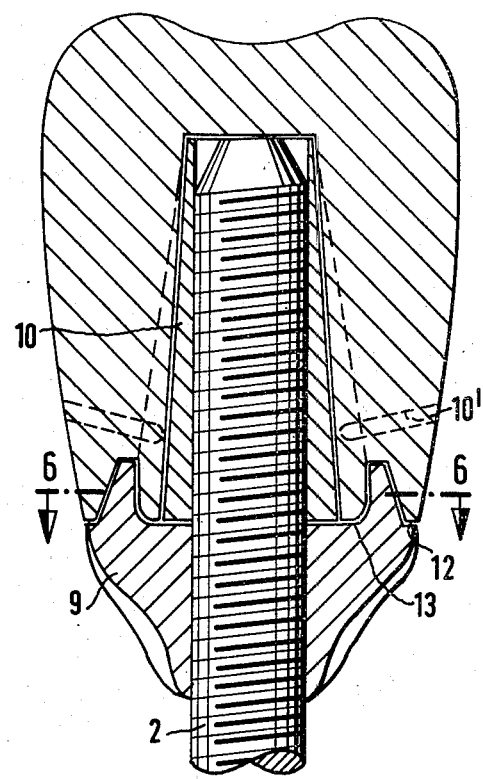
Figure 4:
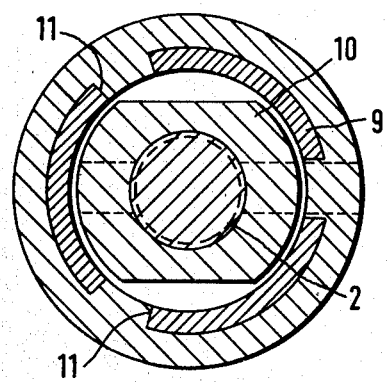
Figure 6:
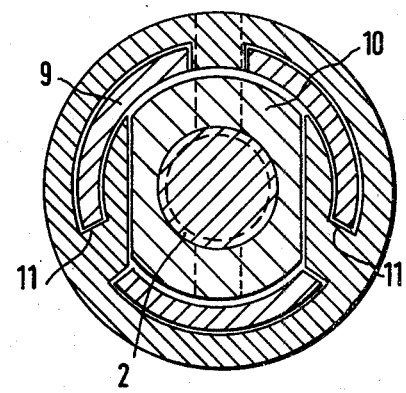
Figure 7:
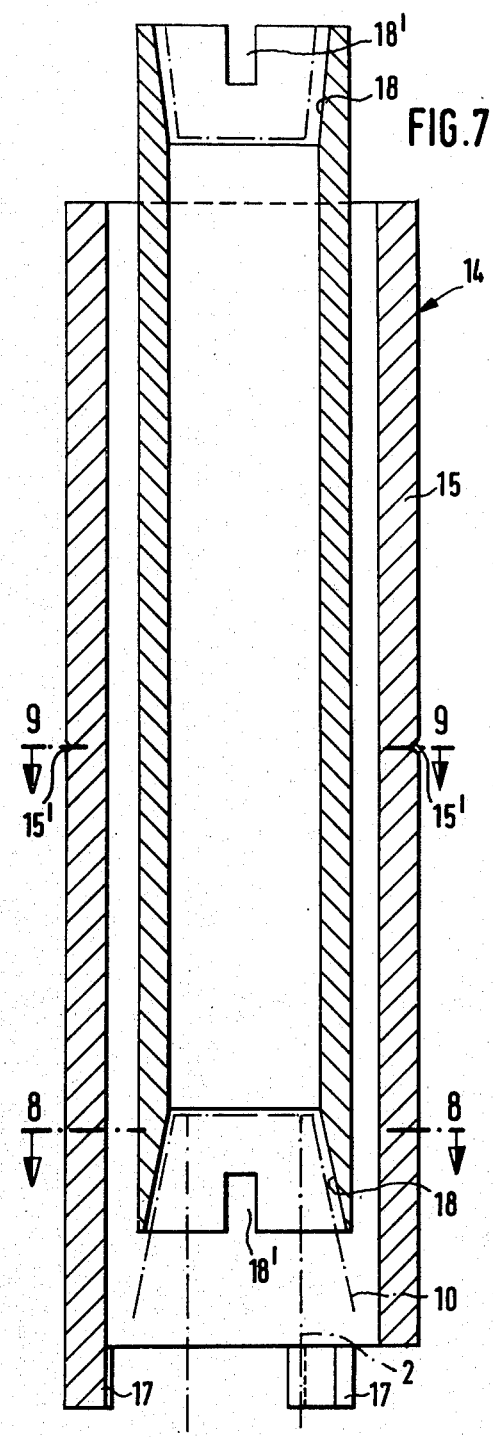
Figure 8:
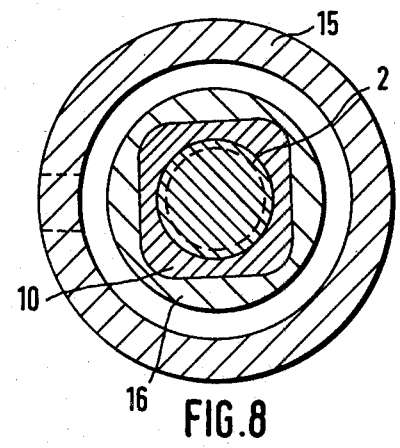
Figure 9:
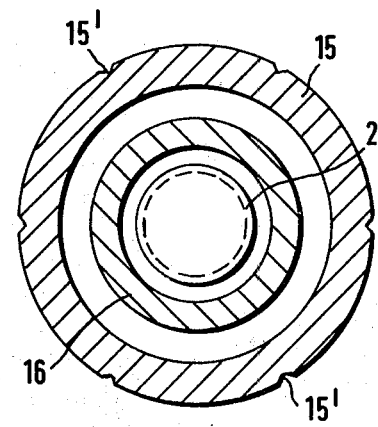

In order that the invention may be more easily understood it is now described on the basis of the adjoining drawings, by way of example only, showing in:

FIGS. 1 and 2 respectively an elevation and an overhead plan view of the base and the shaft of a variable geometry implant according to the invention.

As can be seen in FIGS. 1 and 2 the implant consists of a perforated base 1 with a threaded rod or shaft 2 mounted on top of it. This base 1 is asymmetrical in relation to the shaft, but is formed in such a way that the areas 3 and 4 situated on both sides of the axis XY are equal, although differing in length and width.

In the example shown one of the areas 3 is square in its morphology, and the other 4 is rectangular.

The base 1 has on each of its areas 3, 4 a perforated part 3', 4' different in conformation but with the same surface area. Each of these surfaces is provided at the end with two extensions 5, the surface area of these also being equal on both sides and, they are capable of being bent over, in order to facilitate the fitting of the implant and, subsequently to increase its stability when in place. On the other hand, the dimensions of the base 1 can be reduced either by dispensing with these extensions on both sides, or by removing from the outer edge of the base the two tongues 6,7 the same in area, but distributed differently, the remaining surface thus being left perfectly balanced. The cutting of these extensions and tongues is facilitated by grooves 8 which are provided for this purpose.

The use of implants according to the invention allows for readjustment at the level of the gum at a time of involution and the system of pins, which is particularly suitable in areas at the back when using the lamina implantation, avoids the use of over-strong cements which would hinder secondary manipulation.

The prosthesis fitter, as a result to the base plate, will have each time precise information about the limits of the crowns, which should not be made exclusively of ceramics.

I claim:

1. A variable geometry implant comprising
a base formed with perforations,
a threaded shaft extending from said base,
said base is asymmetrically irregular with respect to the shaft, but in perfect balance with respect to said shaft,
the base has surface areas respectively on both sides of the shaft which are equal but different in shape, and
the perforations on both sides of the shaft are equal in area but different in shape.

2. The implant according to claim 1, wherein
said base has an end on each side of the shaft formed with extensions respectively having the same area and being bendable so as to facilitate fitting of the implant and to increase its stability when in place.

3. The implant according to claim 1, wherein
the surface area on one side of the shaft is square and the surface area on the other side is rectangular.

4. The implant according to claim 1, wherein
said base tapers in plan view from a wider of said surface area on one side of the shaft to a narrower of said surface area on the other side of said shaft.

5. A variable geometry implant comprising
a base formed with perforations,
a threaded shaft extending from said base,
said base is asymmetrically irregular with respect to the shaft, but in perfect balance with respect to said shaft,
the base has surface areas respectively on both sides of the shaft which are equal but different in shape, and
the perforations on both sides of the shaft are equal in area but different in shape,
said base has an end on each side of the shaft formed with extensions respectively having the same area and being bendable so as to facilitate fitting of the implant and to increase its stability when in place,
said base being formed with weakened portions which facilitate removing said extensions so as to reduce the area of the base while simultaneously retaining the perfect balance with respect to said shaft.

6. A variable geometry implant comprising
a base formed with perforations,
a threaded shaft extending from said base,
said base is asymmetrically irregular with respect to the shaft, but in perfect balance with respect to said shaft,
the base has surface areas respectively on both sides of the shaft which are equal but different in shape, and
the perforations on both sides of the shaft are equal in area but different in shape,
said base has an outer edge on each side of said shaft formed with tongues, respectively, which are the same in area and are distributed differently on both sides of the shaft, and said base being formed with weakened portions which facilitate removing said tongues so as to reduce the area of the base while simultaneously retaining the perfect balance with respect to said shaft.

7. The implant according to claim 5 or 6, wherein
said weakened portions define grooves formed in said base.

* * * * *